United States Patent
Liu et al.

(10) Patent No.: US 8,258,331 B2
(45) Date of Patent: Sep. 4, 2012

(54) METHOD FOR PREPARATION OF N-METHYL-3-(2-TRIBUTYL STANNYLPHENOXY)-3-PHENYLPROPANAMINE, AND USE THEROF

(75) Inventors: Show-Wen Liu, Changhua County (TW); Cheng-Hsien Lin, Taipei (TW); Tsyh-Lang Lin, Taoyuan County (TW); Cheng-Fang Hsu, Miaoli County (TW); Yu Chang, Taipei (TW)

(73) Assignee: Institute of Nuclear Energy Research Atomic Energy Council, Executive Yuan, Taoyuan County (TW)

( * ) Notice: Subject to any disclaimer, the term of this patent is extended or adjusted under 35 U.S.C. 154(b) by 0 days.

(21) Appl. No.: 13/087,862

(22) Filed: Apr. 15, 2011

(65) Prior Publication Data

US 2011/0313183 A1 Dec. 22, 2011

(30) Foreign Application Priority Data

Jun. 22, 2010 (TW) .................................. 99120267 A (51) Int. Cl.
*C07F 7/22* (2006.01)
*C07C 217/00* (2006.01)

(52) U.S. Cl. .......................................... 556/87; 564/347
(58) Field of Classification Search .................... 556/87; 564/347
See application file for complete search history.

(56) References Cited

U.S. PATENT DOCUMENTS

2011/0319664 A1* 12/2011 Chen et al. ..................... 564/300

OTHER PUBLICATIONS

Galli et al., Journal of Experimental Biology, vol. 198, pp. 2197-2212 (1995).*
Kiyono et al., Nuclear Medicine and Biology, vol. 31, pp. 147-153 (2004).*
Chumpradit et al., Journal of Medicinal Chemistry, vol. 35, pp. 4492-4497 (1992).*

* cited by examiner

*Primary Examiner* — Porfirio Nazario Gonzalez
(74) *Attorney, Agent, or Firm* — WPAT, PC; Justin King (57) ABSTRACT

A method for preparation of N-methyl-3-(2-tributylstannylphenoxy)-3-phenylpropanamine is provided, which includes formation of N-methyl-3-(2-tributylstannylphenoxy)-3-phenylpropanamine, useful as a precursor of a norepinephrine transporter (NET) contrast label [$^{123}$Iodine](R)—N-methyl-3-(2-iodophenoxy)-3-phenylpropanamine ([$^{123}$I] MIPP) with a leaving group $Bu_3Sn$.

9 Claims, 10 Drawing Sheets

METHOD FOR PREPARATION OF N-METHYL-3-(2-TRIBUTYLSTANNYL PHENOXY)-3-PHENYLPROPANAMINE, AND USE THEROF

BACKGROUND OF THE INVENTION

1. Field of Invention

The present invention relates to a method for preparation of N-methyl-3-(2-tributylstannylphenoxy)-3-phenylpropanamine (MSPP), and particularly to formation of a labeling precursor MSPP with a leaving group $Bu_3Sn$.

2. Related Art

Norepinephrine, together with dopamine and serotonin are three important monoamine neurotransmitters in the brain, and are responsible for regulation of all mental and physical activities. For a long time, it is considered that norepinephrine and a uptake system are closely associated with treatment of neuropsychological disorders, for example, norepinephrine transporter (NET) and serotonin transporter are both useful as anti-depression therapeutic agents (A. Galli et al., *J. Exp. Biol.* 1995, 198: 2197-2212).

Where neurotransporter is imaged in combination with nuclear medicine imaging technology, both Positron Emission Tomography (PET) and Single Photon Emission Computed Tomography (SPECT) can be used in research of treatment opportunities of anti-depression drugs, thus being beneficial to clinical treatment of diseases. At present, contrast media for serotonin include [$^{123}$I]ADAM, [$^{11}$C]MADAM, [$^{11}$C]DASB, and [$^{19}$F]-4-F-ADAM, and so on, but there are fewer contrast media for NET.

For development of nuclear medicine imaging technology of NET, nuclear pharmaceuticals capable of binding to NET need be found. Currently, the most commonly used nuclear pharmaceuticals capable of specifically binding to NET includes earlier desipramine and latter reboxetine and nisoxetine, in which a contrast medium with desipramine as a labeling is radioactive $^{11}$C labeled $^{11}$C-desipramine, and a contrast medium with reboxetine or a structural analogue thereof as a labeling precursor is $^{11}$C-MeNER. Considering that SPECT is one of most commonly used imaging modalities in diagnosis of diseases with nuclear pharmaceuticals at present, it is necessary to develop nuclear pharmaceuticals useful in a SPECT system.

(R)—N-methyl-3-(2-iodophenoxy)-3-phenylpropanamine (MIPP) is obtained by iodinating at Position 2 of a phenyl ring in nisoxetine, and has the chemical structure below:

which is useful as a contrast medium for NET. In 2004, Y. Kiyono suggested in a research that (R)—[$^{123}$I]MIPP has strong selective affinity for NET in brain; moreover, lipophilic property of MIPP enables MIPP to penetrate the blood brain barrier and enter the brain, and thus MIPP is useful as a contrast medium for norepinephrine in brain central nervous system, and is beneficial to research and diagnosis of neuropsychological disorders such as depression (Y. Kiyono et al., *Nucl. Med. Biol.* 2004, 31:147-153).

The scheme for preparing (R)—[$^{123}$I]MIPP is as follows.

(R)—N-methyl-3-(2-bromophenoxy)-3-phenylpropanamine ((R)-MBPP), as a labeling precursor (S. Chumpradit et al., *J. Med. Chem.* 1992, 35: 4492-4497), is subjected to solid-state halogen-exchange reaction with iodide ions at a high temperature of 140° C., and then the resulting product is purified through reverse-phase liquid chromatography (LC). As (R)—[$^{123}$I]MIPP and (R)-MBPP have similar properties, purification is quite time consuming. Therefore, finding a precursor with physical and chemical properties different from those of contrast label (R)—[$^{123}$I]MIPP can facilitate simplification of the preparation process and purification steps.

SUMMARY OF THE INVENTION

The present invention is directed to a method for preparation of N-methyl-3-(2-tributylstannylphenoxy)-3-phenylpropanamine (MSPP), N-methyl-3-(2-tributylstannylphenoxy)-3-phenylpropanamine thus prepared, and a use thereof. Therefore, the present invention provides a method for preparation of N-methyl-3-(2-tributylstannylphenoxy)-3-phenylpropanamine (referred to as MSPP), which comprises:

(1) dehydrating initial reactants 3-chloro-1-phenylpropanol and 2-halophenol, to generate phenylpropane halide;

(2) heating at least one compound of (1) and excessive aqueous methylamine solution to reflux, to generate N-methyl-3-(2-halophenoxy)-3-phenylpropanamine; and (3) subjecting at least one compound of (2) and bis(tributyltin) to a substitution reaction, to generate N-methyl-3-(2-tributylstannylphenoxy)-3-phenylpropanamine.

In some embodiments, the dehydration reaction is carried out in a solvent of tetrahydrofuran or other organic solvents miscible with water, for example, 1,4-dioxane. In a specific embodiment, tetrahydrofuran is used as the solvent.

In a specific embodiment, halo in (1) is bromo or iodo.

In some embodiments, a catalyst for the substitution reaction of (3) is bis(triphenylphosphine)palladium (II) dichloride or tetrakis(triphenylphosphine)palladium (0).

The present invention further provides N-methyl-3-(2-tributylstannylphenoxy)-3-phenylpropanamine thus prepared.

The present invention further provides a labeling precursor of a contrast medium, which comprises N-methyl-3-(2-tributylstannylphenoxy)-3-phenylpropanamine.

In some embodiments, the contrast medium is a NET contrast medium. In a specific embodiment, the contrast medium is (R)—N-methyl-3-(2-iodophenoxy)-3-phenylpropanamine (MIPP).

The present invention further provides a method for improving a labeling yield of a labeling reaction, which comprises:

(1) preparing N-methyl-3-(2-tributylstannylphenoxy)-3-phenylpropanamine following a preparation method according to claim 1;

(2) subjecting N-methyl-3-(2-tributylstannylphenoxy)-3-phenylpropanamine and iodide ions to a substitution reaction, to prepare (R)—N-methyl-3-(2-iodophenoxy)-3-phenylpropanamine; and (3) separating unreacted N-methyl-3-(2-tributylstannylphenoxy)-3-phenylpropanamine from (R)—N-methyl-3-(2-iodophenoxy)-3-phenylpropanamine through liquid chromatography (LC).

The preparation method of the present invention is to simplify separation and purification after reaction of the labeling, by substituting bromo in the original labeling precursor MBPP with a leaving group $Bu_3Sn$, to form a labeling precursor MSPP, and then substituting $Bu_3Sn$ in the labeling precursor with $[*I]^+$ ions, to form a final product MIPP.

Because a leaving group in the labeling precursor MBPP in the prior art is bromo, the leaving degree of bromo in the substitution reaction may be not as high as that of $Bu_3Sn$ used in the preparation method of the present invention; an underlined principle is that those having a lower polarity with increasing carbon atoms are more easily dissolved in a solvent, thus have a good solvent effect, and can easily leave in reaction. Therefore, compared with MBPP, MSPP can be more easily subjected to a substitution reaction in a solution with iodide ions, to generate (R)—$[^{123}I]$MIPP.

Furthermore, according to the method of the present invention for improving the labeling yield of the labeling reaction, the physical and chemical properties of the prepared MSPP is much different from those of MIPP, and thus compared with MBPP, use of MSPP as a precursor of MIPP can be more easily separated and purified, thereby improving the labeling yield and the efficiency of separation and purification.

Details of one or more embodiments of the present invention will be described in details below. Other features and advantages of the present invention will be apparent from detailed description and claims below.

The above general description and the following detailed description can be understood with reference to examples, and provide further illustration of subjects as claimed in the present invention.

BRIEF DESCRIPTION OF THE DRAWINGS

The present invention will become more fully understood from the detailed description given herein below for illustration only, and thus are not limitative of the present invention, and wherein.

DETAILED DESCRIPTION OF THE INVENTION

In order to make features and effects of the present invention clearer and more comprehensible, the present invention is illustrated with reference to preferred embodiments below and appended drawings.

A preparation process of the present invention is provided below.

Initial reactants 3-chloro-1-phenylpropanol and 2-iodophenol or 2-bromophenol are dehydrated in an organic solvent containing diethyl azodicarboxylate, to generate 1-chloro-3-(2-iodophenoxy)-3-phenylpropane (1-A) or 1-chloro-3-(2-bromophenoxy)-3-phenylpropane (1-B); then Compound 1-A or 1-B and excessive aqueous methylamine solution are heated to reflux, to replace chloro on a first carbon of the compound with methylamino, so as to generate a compound MIPP or MBPP respectively; and finally, with bis(triphenylphosphine)palladium (II) dichloride as a catalyst, the compound MIPP or MBPP and bis(tributyltin) are subjected to a substitution reaction, to synthesize a compound MSPP. Steps of the preparation process are described in detail below, and corresponding results are also provided.

Embodiment 1

Synthesis of (R)-(−)-1-Chloro-3-(2-iodophenoxy)-3-phenylpropane (1-A)

2-iodophenol (1.29 g, 5.86 mmole), (S)-(−)-3-chloro-1-phenylpropanol (1.10 g, 5.86 mmole), triphenylphosphine (1.54 g, 5.86 mmole), and diethyl azodicarboxylate (2.7 ml, 5.86 mmole) were dissolved in dry tetrahydrofuran (20 ml), and stirred at room temperature for 4 days. After concentration under vacuum, n-hexane was added (50 ml) for extracting the residue. The extract was concentrated under vacuum, and purified through liquid chromatography, in which a stationary phase was silica ($SiO_2$), and a mobile phase was chloroform:n-hexane=1:20, to obtain the product as an oil (1.44 g, 67.4%).

The chemical structure of the oil product was analyzed through $^1H$ and $^{13}C$ nuclear magnetic resonance (NMR) spectra-mass spectrometry (MS), and the data was as follows.

Figure 1A:
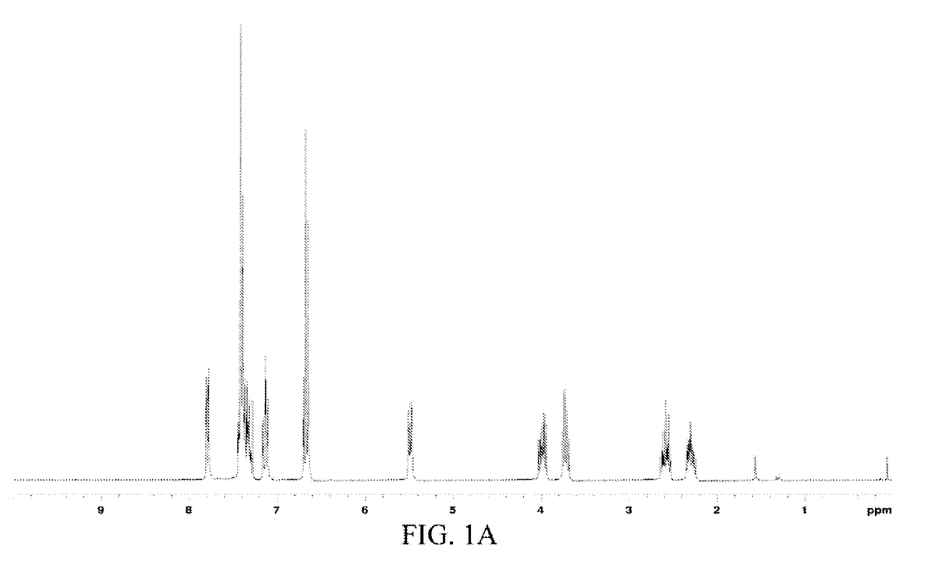
FIG. 1A is $^1$H NMR ($CDCl_3$) spectrum for NMR spectra of Embodiment 1.
Figure 1B:
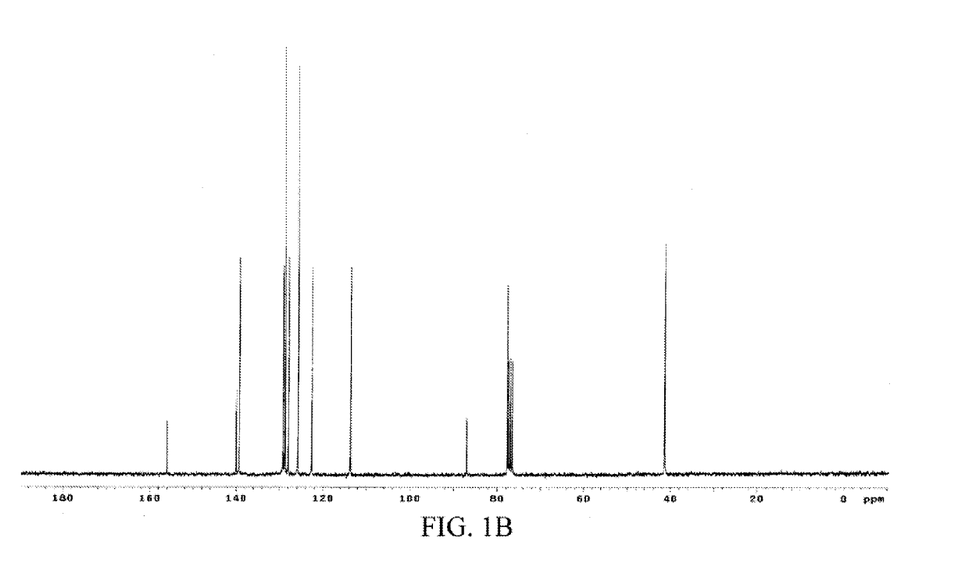
FIG. 1B is $^{13}$C NMR ($CDCl_3$) spectrum for NMR spectra of Embodiment 1.

$^1H$ and $^{13}C$ NMR spectra: $^1H$ NMR ($CDCl_3$) δ 7.81 (dd, J=6.6 and 1.5 Hz, 1H, Ph), 7.33 (m, 5H, Ph), 7.13 (td, J=7.9 and 1.4 Hz, 1H, Ph), 6.70 (m, 2H, Ph), 5.49 (dd, J=8.6 and 4.4 Hz, 1H, $H_1$), 4.0 (m, 1H, $H_2$), 3.74 (m, 1H, $H_2$), 2.58 (m, 1H, $H_3$), 2.29 (m, 1 H, $H_3$). $^{13}C$ NMR ($CDCl_3$) δ 156.04, 140.04, 139.33, 129.19, 128.81, 128.0, 125.82, 122.61, 113.69, 86.98 (Ph), 77.73 (CH), 41.45 and 41.38 ($CH_2CH_2Cl$).

MS: m/z is 374 and 372 ($M^+$).

NMR spectra were as shown in FIGS. 1A and 1B, and the oil product was confirmed to be (R)-(−)-1-chloro-3-(2-iodophenoxy)-3-phenylpropane (1-A) by analyzing the results of NMR spectra-MS.

Embodiment 2

Synthesis of (R)-(−)-1-Chloro-3-(2-bromophenoxy)-3-phenylpropane (1-B)

2-bromophenol (1.29 g, 5.86 mmole), (S)-(−)-3-chloro-1-phenylpropanol (1.0 g, 5.86 mmole), triphenylphosphine (1.54 g, 5.86 mmole), and diethyl azodicarboxylate (2.7 ml, 5.86 mmole) were dissolved in dry tetrahydrofuran (20 ml), and stirred at room temperature for 4 days. After concentration under vacuum, n-hexane was added (50 ml) for extracting the residue. The extract was concentrated under vacuum, and purified through LC, in which a stationary phase was silica ($SiO_2$), and a mobile phase was chloroform:n-hexane=1:20, to obtain the product as an oil (1.42 g, 74.4%).

The chemical structure of the oil product was analyzed through $^1H$ and $^{13}C$ NMR spectra-MS, and the data was as follows.

Figure 2A:
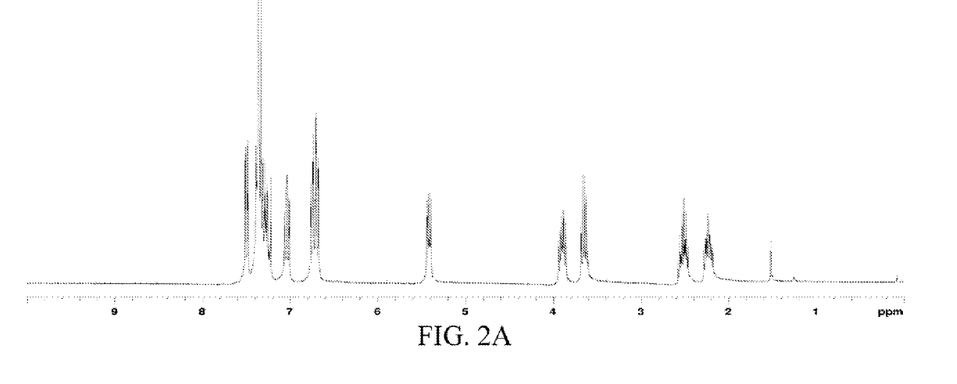
FIG. 2A is $^1$H NMR ($CDCl_3$) spectrum for NMR spectra of Embodiment 2.
Figure 2B:
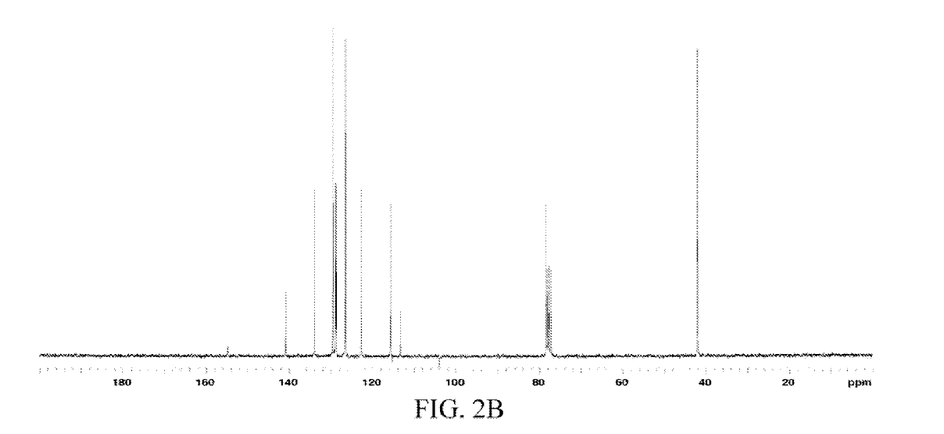
FIG. 2B is $^{13}$C NMR ($CDCl_3$) spectrum for NMR spectra of Embodiment 2.

$^1H$ and $^{13}C$ NMR spectra: $^1H$ NMR ($CDCl_3$) δ 7.50 (dd, J=7.8 and 1.5 Hz, 1H, Ph), 7.33 (m, 5H, Ph), 7.04 (td, J=8.0 and 1.7 Hz, 1H, Ph), 6.71 (m, 2H, Ph), 5.42 (dd, J=8.7 and 4.2 Hz, 1H, $H_1$), 3.89 (m, 1H, $H_3$), 3.65 (m, 1H, $H_3$), 2.50 (m, 1H, $H_2$), 2.22 (m, 1H, $H_2$). $^{13}C$ NMR ($CDCl_3$) δ 154.74, 140.84, 133.94, 129.50, 128.89, 128.72, 126.50, 122.70, 115.66, 113.29 (Ph), 78.45 (CH), 42.03 ($CH_2CH_2Cl$).

MS: m/z is 326 and 324 ($M^+$).

NMR spectra were as shown in FIGS. 2A and 2B, and the oil product was confirmed to be (R)-(−)-1-chloro-3-(2-bromophenoxy)-3-phenylpropane (1-b) by analyzing the results of NMR spectra-MS.

Embodiment 3

Synthesis of (R)-(−)-N-Methyl-3-(2-iodophenoxy)-3-phenylpropanamine (MIPP)

Compound 1-A (2.68 g, 7.2 mmole) was dissolved in an aqueous solution of ethanol (80 ml) and methylamine (160 ml), and heated to reflux for 30 h. After cooling, the solution was extracted with chloroform (100 ml, twice), and an organic layer was decanted. The organic layer was dried over anhydrous sodium sulfate, and dried by evaporation under vacuum, to obtain the product as oil (2.75 g, 97.4%).

The chemical structure of the oil product was analyzed through $^1H$ and $^{13}C$ NMR spectra-MS, and the data was as follows.

Figure 3A:
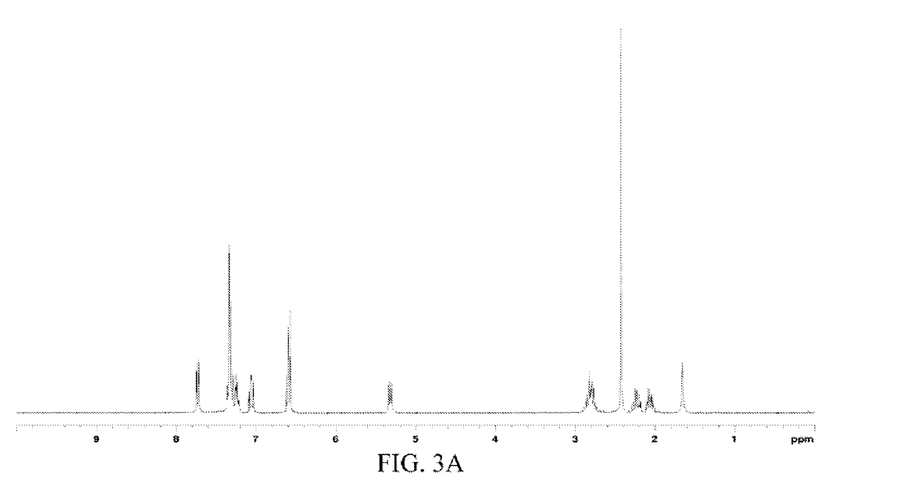
FIG. 3A is $^1$H NMR ($CDCl_3$) spectrum for NMR spectra of Embodiment 3.
Figure 3B:
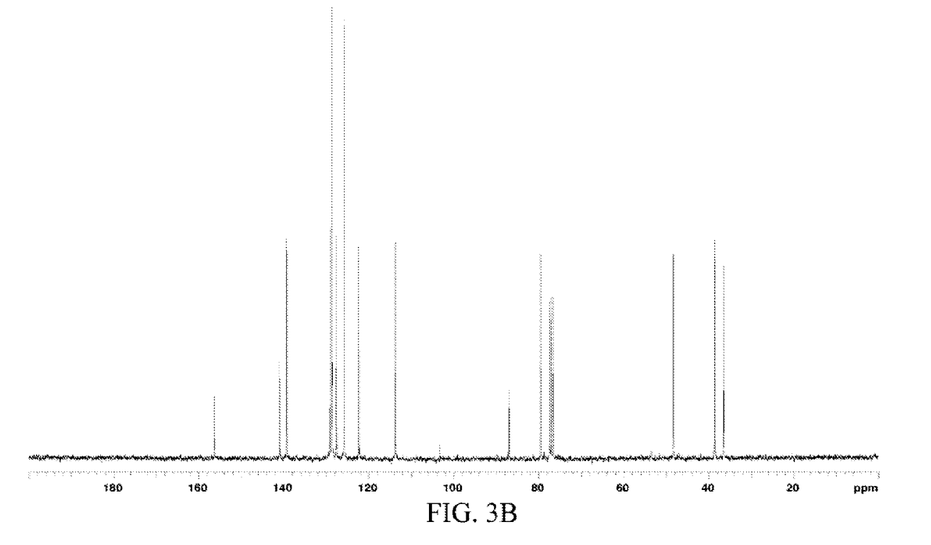
FIG. 3B is $^{13}$C NMR ($CDCl_3$) spectrum for NMR spectra of Embodiment 3.

$^1H$ and $^{13}C$ NMR spectra: $^1H$ NMR ($CDCl_3$) δ 7.73 (dd, J=8.1 and 1.5 Hz, 1H, Ph), 7.31 (m, 5H, Ph), 7.06 (td, J=7.8 and 1.5 Hz, 1H, Ph), 6.60 (m, 2H, Ph), 5.32 (dd, J=8.3 and 4.7 Hz, $H_3$), 2.83 (m, 2H, $H_2$), 2.43 (s, 3H, $H_3$), 2.23 (m, 1H, $H_1$), 2.05 (m, 1H, $H_1$), 1.66 (s, 1H, NH). $^{13}C$ NMR ($CDCl_3$) δ 156.30, 141.01, 139.30, 129.11, 128.63, 127.62, 125.80, 122.34, 113.74 and 87.0 (Ph), 79.52 (CH), 48.33 and 38.59 ($CH_2CH_2N$), 36.49 ($CH_3$).

MS: m/z is 367 ($M^+$), 240 ($M^+$-1).

NMR spectra were as shown in FIGS. 3A and 3B, and the oil product was confirmed to be MIPP by analyzing the results of NMR spectra-MS.

Embodiment 4

Synthesis of (R)-(−)-N-Methyl-3-(2-bromophenoxy)-3-phenylpropanamine (MBPP)

Compound 1-B (1.31 g, 4.02 mmole) was dissolved in an aqueous solution of ethanol (40 ml) and methylamine (80 ml), and heated to reflux for 30 h. After cooling, the solution was extracted with chloroform (100 ml, twice), and an organic layer was decanted. The organic layer was dried over anhydrous sodium sulfate, and dried by evaporation under vacuum, to obtain the product as oil (1.28 g, 99.2%).

The chemical structure of the oil product was analyzed through $^1$H and $^{13}$C NMR spectra-MS, and the data was as follows.

Figure 4A:
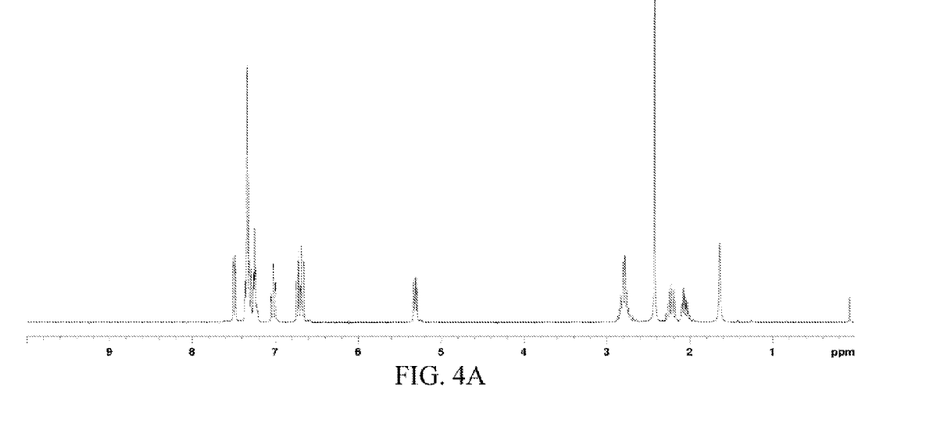
FIG. 4A is $^1$H NMR ($CDCl_3$) spectrum for NMR spectra of Embodiment 4.
Figure 4B:
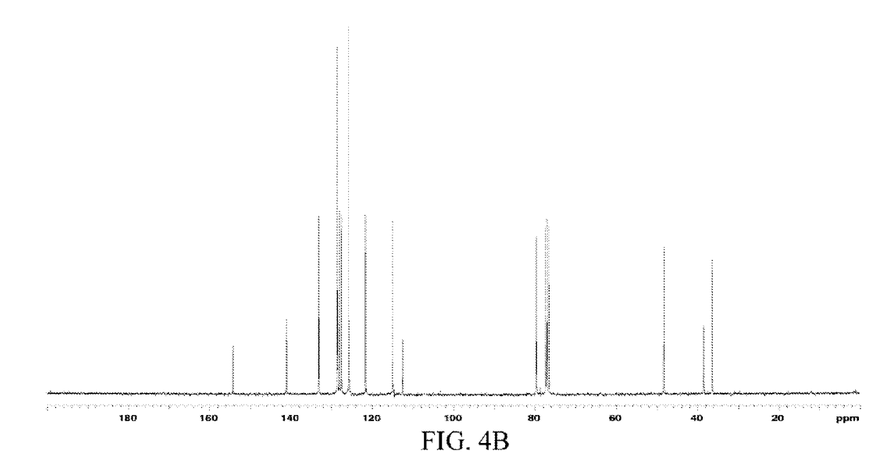
FIG. 4B is $^{13}$C NMR ($CDCl_3$) spectrum for NMR spectra of Embodiment 4.

$^1$H and $^{13}$C NMR spectra: $^1$H NMR (CDCl$_3$) δ 7.49 (dd, J=7.8 and 1.5 Hz, 1H, Ph), 7.29 (m, 5H, Ph), 7.03 (td, J=7.8 and 1.2 Hz, 1H, Ph), 6.72 (m, 2H, Ph), 5.31 (dd, J=8.1 and 4.5 Hz, 1H, H$_3$), 2.81 (m, 2H, H$_2$), 2.43 (s, 3H, CH$_3$), 2.22 (m, 1H, H$_1$), 2.07 (m, 1H, H$_1$), 1.64 (s, 1H, NH). $^{13}$C NMR (CDCl$_3$) δ 154.24, 141.07, 133.19, 128.61, 128.10, 127.64, 125.75, 121.71, 114.99, 112.55 (Ph), 79.66 (CH), 48.31 and 38.53 (CH$_2$CH$_3$N), 36.46 (CH$_3$).

MS: m/z is 321 and 319 (M$^+$), 240 (M$^+$-Br).

NMR spectra were as shown in FIGS. 4A and 4B, and the oil product was confirmed to be MBPP by analyzing the results of NMR spectra-MS.

Embodiment 5

Synthesis of (R)—N-Methyl-3-(2-tributylstannylphenoxy)-3-phenylpropanamine (MSPP)

The compound MIPP (0.34 g, 0.92 mmole), bis(tributyltin) (0.8 ml, 1.6 mmole), and bis(triphenylphosphine)palladium (II) dichloride (0.04 g) were dissolved in dry pyridine (5 ml), and heated to reflux for 120 h (in equipment fitted with a drying tube). After cooling, dichloromethane (50 mL) was added, and filtrated under vacuum. The organic layer was washed with water (100 ml, twice), and the aqueous layer was discarded. The organic layer was dried over anhydrous sodium sulfate, dried by evaporation under vacuum, and purified through LC, in which a stationary phase was silica (SiO$_2$), and a mobile phase was chloroform:n-hexane=1:20, to obtain the product as an oil (0.232 g, 47.8%). With bis(triphenylphosphine)palladium (II) dichloride as a catalyst, the compound MIPP and bis(tributyltin) were subjected to a substitution reaction, to synthesize the product.

The chemical structure of the oil product was analyzed through $^1$H and $^{13}$C NMR spectra-MS, the results obtained from infrared (IR) spectrum was further provided, and the data was as follows.

IR spectrum: IR (Neat) v3381 (NH) cm$^{-1}$.

Figure 5A:
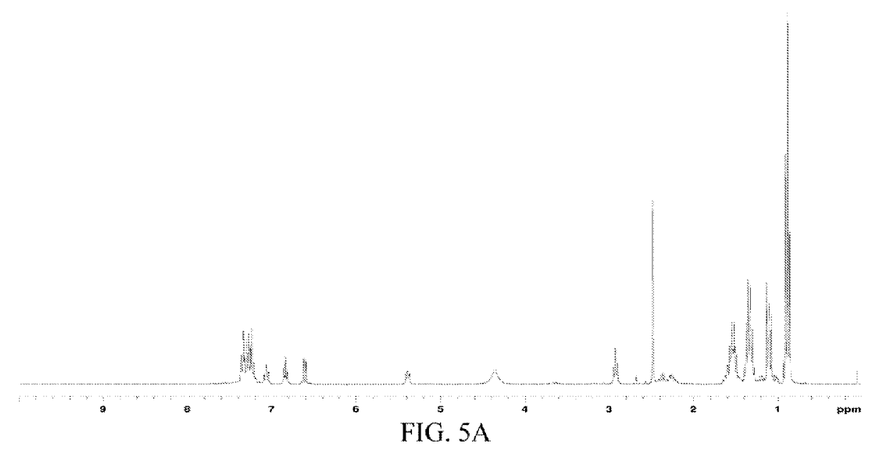
FIG. 5A is $^1$H NMR ($CDCl_3$) spectrum for NMR spectra of Embodiment 5.
Figure 5B:
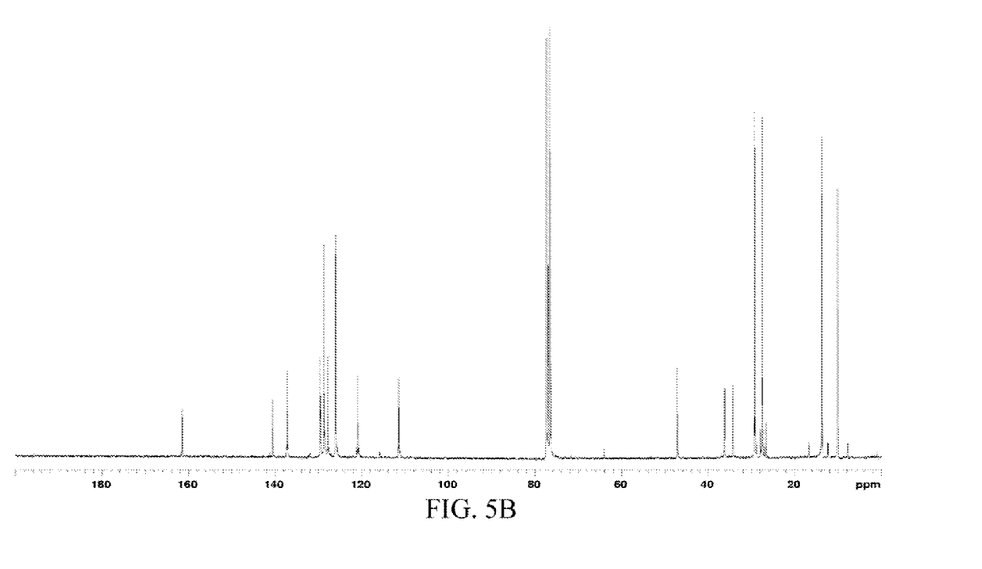
FIG. 5B is $^{13}$C NMR ($CDCl_3$) spectrum for NMR spectra of Embodiment 5.

$^1$H and $^{13}$C NMR spectra: $^1$H NMR (CDCl$_3$) δ 7.30 (m, 6H, Ph), 7.07 (td, J=7.8 and 1.8 Hz, 1H, Ph), 6.84 (t, J=6.9 Hz, 1H, Ph), 6.61 (d, J=8.1 Hz, 1H, Ph), 5.38 (dd, J=7.7 and 5.0 Hz, 1H, CH), 4.36 (br, 1H, NH), 2.93 (t, J=7.2 Hz, 2H, CH$_2$N), 2.48 (s, 3H, NCH$_3$), 2.37 (m, 1H, CH$_2$CH$_2$N), 2.26 (m, 1H, CH$_2$CH$_2$N), 1.53 (m, 6H, SnCH$_2$CH$_2$) (bold, 1.31 (m, 6H, CH$_2$CH$_3$), 1.13 (m, 6H, SnCH$_2$), 0.88 (t, J=7.2 Hz, 9H, CH$_3$). $^{13}$C NMR (CDCl$_3$) δ 161.54, 140.50, 137.21, 129.58, 128.70, 127.82, 126.01, 120.92, 111.43 (Ph), 76.31 (CH), 47.13 and 36.12 (CH$_2$CH$_2$N), 34.27 (CH$_3$), 29.12 (CH$_2$CH$_3$), 27.10 (SnCH$_2$CH$_2$), 13.76 (CH$_3$), 10.02 (SnCH$_2$).

MS: m/z is 531 and 529 (M$^+$), 474 and 472 (M$^+$-Bu), 360 and 358 (M$^+$-3 Bu).

NMR spectra were as shown in FIGS. 5A and 5B, and the oil product was confirmed to be MSPP by analyzing the results of NMR spectra-MS.

Embodiment 6

Separation of MSPP and MIPP

With Microsorb-C18 as a separation column, and 50% methanol (containing 0.2% trifluoroacetic acid) flowing at 0.5 ml/min as a elution solution, the retention time of (R)-MBPP, (R)—[$^{123}$I]MIPP and (R)-MSPP is respectively 27, 34, and 73 min. Therefore separation and purification can be easily implemented in case that MSPP, instead of MBPP, is used as a precursor of MIPP, and the labeling yield and the efficiency of separation and purification through is improved.

Other Embodiments

All features disclosed in the specification can be combined in any manner, and each feature can be replaced by the same, equivalent, or similar alternative features. Therefore, unless specified otherwise, each feature disclosed herein is merely an example of a wide series of the same or similar features. Based on the description, necessary features of the present invention can be easily recognized by persons skilled in the art, and various alternations and modifications for various uses or situations can be achieved without departing from the spirit and scope of the present invention. Therefore, other embodiments are still within the scope of the claims of the present invention.

All patents and publications mentioned in the specification indicate the knowledge degree of persons of ordinary skill in the art. All patents and publications mentioned in the specification are incorporated herein by reference in their entirety, and each patent or publication should be construed as independently incorporated herein by reference in its entirety clearly.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for preparation of N-methyl-3-(2-tributylstannylphenoxy)-3-phenylpropanamine (MSPP), comprising:
   (1) dehydrating initial reactants 3-chloro-1-phenylpropanol and 2-halophenol, to generate phenylpropane halide;
   (2) heating at least one compound of (1) and excessive aqueous methylamine solution to reflux, to generate N-methyl-3-(2-halophenoxy)-3-phenylpropanamine; and
   (3) subjecting at least one compound of (2) and bis(tributyltin) to a substitution reaction, to generate N-methyl-3-(2-tributylstannylphenoxy)-3-phenylpropanamine.

2. The preparation method according to claim 1, wherein in the dehydration reaction in Step (1), tetrahydrofuran or 1,4-dioxane is used as a solvent.

3. The preparation method according to claim 1, wherein halo in (1) is bromo or iodo.

4. The preparation method according to claim 1, wherein a catalyst in the substitution reaction of (3) is bis(triphenylphosphine)palladium (II) dichloride or tetrakis(triphenylphosphine)palladium (0).

5. N-methyl-3-(2-tributylstannylphenoxy)-3-phenylpropanamine prepared following the preparation method according to claim 1.

6. A labeling precursor of a contrast medium, comprising N-methyl-3-(2-tributylstannylphenoxy)-3-phenylpropanamine according to claim 5.

7. The labeling precursor of a contrast medium according to claim 6, wherein the contrast medium is a norepinephrine transporter (NET) contrast medium.

8. The labeling precursor of a contrast medium according to claim 7, wherein the contrast medium is (R)-N-methyl-3-(2-iodophenoxy)-3-phenylpropanamine (MIPP).

9. A method for improving a labeling yield of a labeling reaction, comprising:
(1) preparing N-methyl-3-(2-tributylstannylphenoxy)-3-phenylpropanamine following a preparation method according to claim 1;
(2) subjecting N-methyl-3-(2-tributylstannylphenoxy)-3-phenylpropanamine and iodide ions to a substitution reaction, to prepare (R)-N-methyl-3-(2-iodophenoxy)-3-phenylpropanamine; and
(3) separating unreacted N-methyl-3-(2-tributylstannylphenoxy)-3-phenylpropanamine from (R)-N-methyl-3-(2-iodophenoxy)-3-phenylpropanamine through liquid chromatography (LC).

* * * * *